United States Patent [19]

Winicov et al.

[11] 4,271,149
[45] Jun. 2, 1981

[54] GERMICIDAL IODINE COMPOSITIONS WITH ENHANCED IODINE STABILITY

[75] Inventors: Murray W. Winicov, Woodside, N.Y.; Michael Oberlander, Kansas City, Mo.

[73] Assignee: West Agro-Chemical, Inc., Westwood, Kans.

[21] Appl. No.: 77,787

[22] Filed: Sep. 21, 1979

[51] Int. Cl.$^3$ ............... A01N 59/12; A61K 31/74; A61K 31/79; A61K 33/18

[52] U.S. Cl. ............... 424/150; 424/78; 424/80

[58] Field of Search ............ 424/78, 80, 150

[56] References Cited

U.S. PATENT DOCUMENTS

| | | | |
|---|---|---|---|
| 1,280,580 | 10/1918 | Swett | 424/150 |
| 1,925,135 | 9/1933 | Chandler | 424/150 |
| 1,964,518 | 6/1934 | Karns | 424/150 |
| 2,386,252 | 10/1945 | Mendelsohn | 424/150 |
| 2,918,400 | 12/1959 | Loonam | 424/150 |
| 2,987,505 | 6/1961 | Werner | 260/77.5 |
| 3,288,708 | 11/1966 | Cordle et al. | 424/150 |
| 3,644,650 | 2/1972 | Sabatelli et al. | 424/150 |
| 4,113,857 | 9/1978 | Shetty | 424/150 |

FOREIGN PATENT DOCUMENTS 414951 12/1966 Switzerland ............... 424/78

*Primary Examiner*—Douglas W. Robinson
*Attorney, Agent, or Firm*—Howard E. Thompson, Jr.

[57] ABSTRACT

New and improved germicidal iodine compositions are provided in which iodine levels, in the presence of organic adjuvants containing at least carbon, hydrogen and oxygen atoms, are maintained for extended periods of time in the presence of iodide, through the addition of iodate and control of pH within the range of pH 5–7.

10 Claims, No Drawings

GERMICIDAL IODINE COMPOSITIONS WITH ENHANCED IODINE STABILITY

This invention relates to new and improved iodine germicidal compositions in which iodine levels, in the presence of organic adjuvants containing at least carbon, hydrogen, and oxygen atoms, are maintained over a period of time in the presence of iodide, through the addition of iodate and pH maintenance in the range of pH 5-7.

The purpose of this invention is to provide iodine compositions of greatly increased elemental iodine stability on storage, where the elemental iodine is formulated with adjuvants such as organic detergents, solvents, foam stabilizers, thickeners, buffering agents or the like, that contain carbon, hydrogen, and oxygen atoms (and which may also contain other atoms such as nitrogen, phosphorus, sulfur, etc.). In such compositions the elemental iodine concentration almost always decreases on storage, frequently decreasing much beyond the acceptable amounts allowed for labelling purposes. This invention teaches how the elemental iodine levels can be maintained by the addition of iodate and maintaining the pH in the range of ph 5-7. This teaching is particularly valuable in situations where it is desirable to maintain elemental iodine at levels below 1%, and as low as about 0.01%.

The detergent-iodine literature, mostly consisting of patents and product labels, contains many examples of germicidal iodine products containing 0.5 to 20% iodine. There are hardly any instances of iodine products containing only 0.1% iodine or less. There are two very good reasons for this gap. The first reason is that almost all iodine products offered for sale are in reality concentrates of one type or another. The directions for use ordinarily call for dilution with water, —usually dilutions in the range of 1:100 to 1:1000 with water, so as to provide anywhere from a few ppm of titratable iodine to perhaps 150 ppm iodine at the use-dilution. After use, the diluted product is discarded, since the iodine content of the dilution is only stable for hours, not for weeks or months. For any product intended to be used after dilution with water, it pays to make the product iodine level concentrated, rather than dilute, so that the product is "economical" in view of the final use, in order to compete with other germicidal substances.

The second reason that detergent-iodine products rarely contain 0.1% iodine or less is that it was and is (until now) virtually impossible to maintain a guaranteed amount of iodine at such a low level. For example, a typical iodine product with a label statement guaranteeing 1.6% iodine will ordinarily contain about 1.8% iodine or more when it is manufactured, and it may drop to as low as 1.5% iodine two years after it was manufactured. If the same product, with the same detergent content was prepared with only 0.1% iodine at the start, the iodine content would probably drop to 0% within a few weeks, —certainly within a few months, through slow reaction of the iodine with the organic components of the formulation.

There are certain types of iodine products which are ordinarily not diluted prior to use—such as hand washing compositions, bovine teat dip products to prevent mastitis, and products for topical application. Such products frequently do not require high iodine content for effectiveness, yet formulators find that they have to put in much more than is needed so that the iodine that is lost is an acceptable amount based on the percentage of loss relative to the amount specified on the label. For example, if the organic constituents of an iodine product will react with about 0.2% iodine over the shelf life of the product, and if E.P.A. or F.D.A. label requirements dictate that the product have no more than 110%, and no less than 90% of the labelled amount of iodine active ingredient, then a formulator is forced to set the labelled iodine level at no less than 1.0%, since only then could he manufacture at 1.10%, and end up as low as 0.9% at the end of the guaranteed shelf life, a 0.2% drop in iodine content, while remaining within the regulatory agency requrements. In reality the 1% iodine in the product could be ten times or more iodine than is necessary for the purpose of efficacy.

In the case of the bovine teat dip, the extra iodine, over what is needed for efficacy, is a problem in that it needlessly contributes to iodine levels in milk through skin absorption or through improper teat washing before milking.

In the case of a hand washing composition, the extra iodine contributes to unattractive color, attacks jewelry (rings, etc.) on the hands, and frequently leaves a temporary yellow color on the skin.

It is well known that iodate and iodide react in the presence of hydrogen ions to yield elemental iodine and water according to the equation:

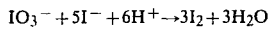

$$IO_3^- + 5I^- + 6H^+ \rightarrow 3I_2 + 3H_2O$$

It is also well known that this reaction is very fast at low pH, e.g. pH 1, 2, or even 3, and that it is slowed down at higher pH values, becoming almost non-reactive at pH 7 and above. Certain dry compositions containing an iodate, an iodide and excess solid acid have been proposed as a means of providing iodine itself at the time of solution in water. The purpose of this invention is to use this reaction to provide very slow release of iodine—so slow that it has never been used before for this purpose—to counterbalance the slow loss of iodine in iodine compositions that contain organic water soluble substances.

The compositions of this invention contain elemental iodine in an amount that usually does not exceed 1%, but is more generally in the range of 0.01% to 0.25% iodine; iodide ion (from any source) preferably in the range of 0.05% to 0.5%; iodate ion (from any source), at least 0.005%, preferably in the range of 0.05% to 0.1%, an organic substance or substances (detergent or solvent, for example) which contains C, H, anc O atoms in an amount from 1 to 50%, and pH control, usually accomplished by the inclusion of a buffering agent (citrate, phosphate, etc.) capable of maintaining a pH in the range of 5 to 7.

The maintenance of the pH in the narrow range of 5 to 7 is the essence, since below pH 5, the reaction of iodate and iodide has been found to proceed too fast to be of value for the purpose of this invention and would generate iodine faster than necessary, resulting in too high an elemental iodine level, too rapid depletion of iodate, and ultimately no counterbalance of iodine loss through iodine regeneration.

The range of iodide concentration of this invention is not characterized by sharp limits. The lower preferred range limit of 0.05% represents an amount which ordinarily must be present in order to provide a sufficient amount to react with the iodate. The upper preferred limit provides both a large "reservoir" to be drawn from, and the higher concentration necessary when large amounts of iodine have to be replenished, or with higher buffered pH, closer to pH 7, when a higher iodide concentration is desired to increase the rate of iodine formation.

The range of iodate ion, from any source, should start at about 0.005%, so that it can provide, ultimately about 0.02% extra iodine in a formulation. For most practical applications, an amount of 0.05-0.10% can be used. Higher amounts can be used, dictated by economics.

The organic substance is an integral part of this invention in that all the uses contemplated concern maintaining the concentration of elemental iodine in an aqueous medium containing organic substances such as a solvent, an iodine solubilizer, an iodine complexing agent, etc., detergent, or the like. Elemental iodine reacts more or less with all such organic substances which contain carbon, hydrogen, and oxygen ("C, H, and O"). Unless such C, H, O containing substance is present, there is no need for this invention. This invention is applicable to essentially all previous aqueous "complexed iodine" art typified by the subject matter in U.S. Pat. Nos. 2,931,777; 2,759,869; 3,028,299; 3,028,300 and many others.

Examples of solvents containing C, H, and O ordinarily used with iodine are ethanol, propanol, isopropanol, propylene glycol, glycerine, polyethylene glycol. These are given by way of illustration, not limitation.

Examples of surface active agents containing C, H, and O ordinarily used with iodine are ethoxylates of alkylphenols, of moderate length alcohols, of polyoxypropylene, anionic detergents that are sulfated, sulfonated, phosphated, carboxylated etc. These, too, are given by way of illustration, not limitation.

Similarly, this invention can be practiced with iodine in combination with other C, H, and O containing substances such as cationic substances and amphoteric substances. The specific organic substance containing C, H, and O is of no importance to this invention. It makes no difference whether the iodine is strongly complexed, weakly complexed, or not complexed at all.

Rather, the need for this invention will be most apparent for weakly complexed iodine compositions, since these generally show greater iodine losses while standing on the shelf compared with strongly complexed iodine.

EXAMPLE 1

A series of iodine compositions were prepared with and without addition of iodate. The samples were stored for a time period up to one week, in glass bottles, at room temperature (20°-25° C.) and at 50° C. for conventional accelerated storage to simulate extended storage at room temperature. As soon as a non-iodate old art composition (e.g. 1A, 2A, etc.) lost all its iodine in the 50° C. oven, the iodate containing counterpart (e.g. 1B, 2B, etc.) was removed and analyzed. After the last of the "A" series samples failed, less than one week from the start of the 50° C. storage, all the room temperature samples were analyzed and the results recorded.

(See Table I)

The results indicate a dramatic improvement in iodine stability in the "B" series compared with the old art "A" series as a direct result of adding iodate to the formulations over the pH range of about 6 through 7. The "A" series lost noticeably more iodine than the "B" series even after only one week at room temperature.

The compositions of Example 1 contain glycerine, propylene glycol, polyethylene glycol 400 (PEG 400), and citric acid as the C, H, O containing organic substances that tend to react with iodine. In this particular example, no surface active substances have been included so as to show that the new teaching extends beyond applications to detergent-iodine complexation art.

We have found that the rate at which a given amount of iodide and iodate react at a particular hydrogen ion concentration is not the same in the presence of C, H, and O containing substances compared with the same concentrations of iodide, iodate, and hydrogen ions in pure water.

TABLE I

| Ingredient | 1A | 1B | 2A | 2B | 3A | 3B | 4A | 4B | 5A | 5B |
|---|---|---|---|---|---|---|---|---|---|---|
| Glycerine | 50.0% | 50.0% | None | None | None | None | None | None | 10.0% | 10.0% |
| Propylene Glycol | None | None | 50.0% | 50.0% | None | None | 10.0% | 10.0% | None | None |
| PEG 400 | None | None | None | None | 50.0% | 50.0% | None | None | None | None |
| Iodine | 0.1% | 0.1% | 0.1% | 0.1% | 0.1% | 0.1% | 0.1% | 0.1% | 0.1% | 0.1% |
| Sodium Iodide | 0.25% | 0.25% | 0.25% | 0.25% | 0.25% 0.25 | 0.25% | 0.25% | 0.25% | 0.25% | |
| Sodium Iodate | None | 0.20% | None | 0.20% | None | 0.20% | None | 0.20% | None | 0.20% |
| Citric Acid | 1.0% | 1.0% | 1.0% | 1.0% | 1.0% | 1.0% | 1.0% | 1.0% | 1.0% | 1.0% |
| Sodium Hydroxide | qs pH 6.2 | pH 6.2 | pH 6.7 | pH 6.7 | pH 6.7 | pH 6.7 | pH 6.3 | pH 6.3 | pH 6.3 | pH 6.3 |
| Water | qs 100% | qs 100% | qs 100% | qs 100% | qs 100% | qs 100% | qs 100% | qs 100% | qs 100% | qs 100% |
| Initial Iodine Content | 0.10% | 0.10% | 0.10% | 0.10% | 0.10% | 0.10% | 0.10% | 0.10% | 0.10% | 0.10% |
| Iodine Content Oven Storage 50° C. | 0.00% | 0.04% | 0.00% | 0.04% | 0.00% | 0.07% | 0.00% | 0.07 | 0.00% | 0.08% |
| Iodine Content Room Temperature (one week) | 0.08% | 0.10% | 0.08% | 0.10% | 0.07% | 0.10% | 0.07% | 0.10% | 0.08% | 0.10% |

The situation becomes rather complicated in that when C, H, and O containing substances are present, these substances react with the iodine already present in the composition. When the iodine compositions contain organic substances that are more reactive, iodine losses can be best balanced by (A) lowering the pH in the range pH 5-7,
(B) using more iodide, and
(C) using more iodate.

These parameters can be varied one at a time, two at a time, or all three together. When the iodine compositions contain less "C, H, O" organic substances, or organic substances that are only slightly reactive with iodine, then less iodide can be used if desired, less iodate, and a higher pH, in the range 5-7. Within the range of pH 5-7, there is an optimum pH to most closely balance iodine loss through formation of iodine in situ from the iodide and iodate in the iodine compositions of this invention. This optimum is usually within the preferred range, pH 5.5-6.5.

The compositions of Example 1, or similar compositions containing more or less glycerine, propylene glycol, PEG 400, or the like, are suitable for use in dipping cows' teats after milking as a mastitis preventative. The iodine in the composition is less firmly complexed than in typical iodine teat dip formulations containing about 1% iodine 0.4% iodide, and about 10% of a nonionic detergent. Less complexed iodine will kill bacteria faster than more complexed iodine. More important, the total iodine content in the Example 1 compositions is less than 0.5%, compared with about 1.5% for conventional 1% elemental iodine teat dips, making the Example 1 compositions less of a hazard with respect to possibly inadvertently contaminating milk with iodine.

efficacy of this composition can not be guaranteed past about one month. Composition 2B, with no iodide in the sample other than the small amount formed from iodine as it reacts with organic matter, is likewise not suitable for sale. In other experiments we have noted that at least about 0.025% by weight of iodide ion must be present in order to be able to keep iodine generated in a meaningful amount by means of iodate. Composition 2C is an example showing borderline utility, owing to a minimum level of iodate. There is only about 0.0088% iodate ion in this composition, which soon becomes too depleted to serve as a reserve for satisfactory continued iodine generation. Composition 2D is shown as an example where either the iodide or iodate concentration should be lowered a little in order to avoid the slight iodine excess.

TABLE II

| Ingredient | A | B | C | D | E | F | G | H | I |
|---|---|---|---|---|---|---|---|---|---|
| Lauryl Sulfate, NH4 Salt | 5.0% W/W | 5.0% | 5.0 | 5.0 | 5.0 | 5.0 | 5.0 | 5.0 | 5.0 |
| Lauric Diethanolamide | 2.0% | 2.0 | 2.0 | 2.0 | 2.0 | 2.0 | 2.0 | 2.0 | 2.0 |
| Iodine | 0.05% | 0.05 | 0.05 | 0.05 | 0.05 | 0.05 | 0.05 | 0.05 | 0.05 |
| Sodium Iodide | 0.25% | None | 0.25 | 0.25 | 0.10 | 0.25 | 0.25 | 0.25 | 0.25 |
| Sodium Iodate | None | 0.05 | 0.01 | 0.20 | 0.20 | 0.05 | 0.05 | 0.05 | 0.05 |
| Citric Acid | 1.0% | 1.0% | 1.0% | 1.0% | 1.0 | 1.0 | 1.0 | 1.00 | None |
| Sodium Hydroxide | qs pH 6.5 | pH 6.5 | pH 6.5 | pH 6.5 | pH 6.5 | pH 6.5 | pH 7.0 | pH 7.5 | pH 6.5 |
| Water | qs 100% | 100% | 100% | to 100% | to 100% | to 100% | to 100% | to 100% | to 100% |
| Initial Iodine Content | 0.05% | 0.05% | 0.05% | 0.05% | 0.05% | 0.05% | 0.05% | 0.05% | 0.05% |
| Final Iodine Content Ambient | 0.002 | 0 | 0.008 | 0.065 | 0.037 | 0.026 | 0.006 | 0 | 0.025 |
| 35° C. | 0 | 0 | 0.002 | 0.070 | 0.035 | 0.020 | 0.002 | 0 | 0.020 |

The compositions of Example 1 may be modified by the addition of thickeners and iodine complexing agents such as ethoxylated detergents, PVP, quaternary amonium compounds, amphoteric detergents, etc., to achieve any desired level of iodine complexing. Whatever the final composition, the desired elemental iodine level can be maintained through addition of iodate and maintenance of pH in the range of 5-7.

EXAMPLE 2

A series of iodine compositions were prepared, suitable for hand washing to remove and kill transient bacteria, with and without addition of iodate. The samples were stored for two weeks at ambient temperature (21°-26° C.) and at 35° C. in glass containers to simulate extended product storage at ambient temperature. Iodine was determined before and after storage. In these compositions, it has been found that as little as 0.002% elemental iodine will surpass the performance of 50 ppm of chlorine by the A.O.A.C. "Available Chlorine Germicidal Equivalent Concentration Test". It has been customary to use iodine compositions for hand washing that contain 0.75 to 1.0% elemental iodine, obviously a gross excess over the amount needed for killing transient bacteria. Iodine hand washing compositions containing about 0.1% elemental iodine or less, will find greater consumer acceptance since there is less yellow color, less odor, less staining, etc. For this purpose, an iodine content anywhere from 0.1% to 0.01% elemental iodine is satisfactory. The most suitable compositions will center around 0.025%, which gives a dark, straw colored product with an almost colorless lather.

(See Table II)

Composition 2A is not considered as an example of this invention since there is no iodate present. Rather it represents the prior art, an example in which the iodine has dropped from 0.050% to 0.002% at ambient temperature (21°-26° C.) after two weeks. Since there is no iodine present in the 35° C. sample, this means that the Alternatively, the pH could be raised to close to pH 7.0. Compositions 2E and 2F are typical examples of satisfactory compositions which although not exactly the same strength as originally made, are stable. Compositions 2G and 2H are a pair to show that pH 7.0 is borderline and pH 7.5 is useless, even though the hydrogen ion concentration difference is very small. Composition 2I, with no buffer added performs as well as its buffered counterpart, 2F. However, this is only because the pH was still 6.3 at both temperatures, without the buffering. In situations where there is the possibility of the pH being significantly disturbed, buffering is essential. Additional compositions, not shown here, using lactate, and phosphate buffer, gave the same results. Below pH 5, it is virtually impossible to control the generation of iodine from added iodate. In terms of the purpose of this invention, iodine is generated too rapidly to be of any use. At pH 5 and above, to pH 7, judicious choice of iodide and iodate can solve the stability problem.

EXAMPLE 3

A series of iodine compositions were prepared, suitable for teat dipping of dairy cows, as a mastitis preventative, with and without the addition of iodate. The samples were stored for two weeks in glass containers at 50° C. to simulate extended product storage at ambient temperature, and were analyzed for iodine at the end of this period.

INGREDIENT (See Table III)

The compositions of Example 3 which are not covered by this invention are the compositions with no iodate, namely 3A, 3C, 3E and 3G. The first composition, 3A, would be acceptable as a product even with an iodine loss of 0.2% over two weeks at 50° C., roughly equivalent to a year at ambient temperature, since it could be released at 1.1% and it would then fall to 0.9%, an acceptable loss. Composition 3C could probably not be sold as a teat dip, since the iodine loss over the accelerated test period was 0.2%, or 40% on a relative basis, compared with the original value. Compositions E and G are unthinkable as products.

However, the same compositions with iodate levels of 0.05 to 0.20%, compositions 3B, 3D, 3F and 3H, are distinctly improved from an elemental iodine stability standpoint; and compositions such as 3F and 3H would offer special advantage as teat dips with very low danger of inadvertent milk contamination possibility.

Below pH 5, at pH 4.5 for example, it is not practicable to add iodate, since iodine concentration in the teat dip formula has been found to actually increase on standing.

Every detergent or iodine carrier or complexer that is acceptable as a component in an aqueous elemental iodine composition, can also be used for the purpose of this invention, and the resultant composition can be shown to have improved iodine stability after addition of iodate and pH adjustment in the range pH 5–7.

TABLE III

| Ingredient | A | B | C | D | E | F | G | H |
|---|---|---|---|---|---|---|---|---|
| Pluronic P85 | 9.56 | 9.56 | 9.56 | 9.56 | 9.56 | 9.56 | 9.56 | 9.56 |
| Citric Acid | 0.5% | 0.5 | 0.5 | 0.5 | 0.5 | 0.5 | 0.5 | 0.5 |
| Iodine | 1.0% | 1.0 | 0.5 | 0.5 | 0.25 | 0.25 | 0.10 | 0.10 |
| HI (100% basis) | 0.45 | 0.45 | 0.2 | 0.2 | 0.1 | 0.1 | 0.04 | 0.04 |
| Sodium Iodate | None | 0.20 | None | 0.20 | None | 0.20 | None | 0.05 |
| Glycerine | 10.0 | 10.0 | 10.0 | 10.0 | 10.0 | 10.0 | 10.0 | 10.0 |
| Sodium Hydroxide | qs pH 5.8 | pH 5.8 | pH 5.6 | pH 5.6 | pH 5.6 | pH 5.6 | pH 5.0 | pH 5.0 |
| Water | to 100% | to 100 | to 100 | to 100 | to 100 | to 100 | to 100 | to 100 |
| Initial Iodine Content* | 1.0 | 1.0 | 0.5 | 0.5 | 0.25 | 0.25 | 0.11 | 0.10 |
| Final Iodine Content* | 0.8 | 1.0 | 0.3 | 0.5 | 0.10 | 0.25 | 0.01 | 0.10 |
| Final pH | 5.6 | 5.6 | 5.6 | 5.6 | 5.6 | 5.5 | 5.0 | 5.0 |

*Samples A - D reported to nearest 0.1%; samples E & F reported to nearest 0.05%; G and H to nearest 0.01%.
Pluronic P85: An ethoxylated polyoxypropylene blood polymer with an average molecular weight in the range of about 5,000.

Because the nature and amounts of organic compounds containing carbon, hydrogen and oxygen and of other adjuvants can be so widely varied, it is difficult to define the invention in terms of amounts, or ranges of amounts, of components. This presents no problem to those wishing to use this invention as for any particular iodine composition desired to be marketed the optimum levels of iodide ion and iodate ion concentrations and the optimum pH adjustment within the range pH 5–7 can be determined by making a few comparisons of the type presented herein, particularly in Example 2. Although looking for iodine stability over an extended period of months or years, meaningful indications of the long range, ambient temperature stability are obtainable by "accelerated aging" as for example storing for two weeks at 50° C., or at some other temperature and time considered appropriate for the particular composition and its intended use.

It should also be noted that it is not essential to the successful practicing of this invention that the iodine level remain the same throughout an extended period of storage. Rather, what is important is that any change in iodine concentration be held within the limits of variation permissible for the particular type product.

Thus germicidal iodine solutions considered to be within the scope of the present invention are those in which optimum selections of iodide and iodate ion concentrations and pH within the pH 5 to 7 range for a particular composition are such that the iodine level during extended storage will remain within the range of variation permissible for such composition.

Various changes and modifications in the germicidal iodine compositions herein disclosed may occur to those skilled in the art, and to the extent that such changes and modifications are embraced by the appended claims, it is to be understood that they constitute part of the present invention.

We claim:

1. A germicidal iodine composition comprising an aqueous solution of elemental iodine in a germicidally effective amount not exceeding about 1.0% and at least one organic substance which slowly reacts with iodine selected from the group consisting of iodine complexing polymers, surface active agents, alcohols, polyols and water soluble solvents, said organic substance constituting 1 to 50% by weight of said composition, wherein iodine loss during extended storage due to such reaction is controlled by providing in said composition balanced sources of iodide ion in the range of about 0.025% to 0.5% and iodate ion in the range of about 0.005% to 0.2% while maintaining a pH within the range of pH 5–7.

2. A germicidal iodine composition as defined in claim 1 wherein the pH is controlled within the range pH 5.5–6.5.

3. A germicidal iodine composition as defined in claim 1, wherein control of pH is enhanced by including a buffering agent.

4. A germicidal iodine composition as defined in claim 1, wherein the amount of elemental iodine is within the range of 0.01 to 0.25%.

5. A germicidal iodine composition as defined in claim 1, wherein said organic substance comprises at least one adjuvant selected from the group consisting of surface active substances, foam stabilizers, complexing agents, thickeners and solvents.

6. A germicidal iodine composition as defined in claim 5, wherein adjuvants are selected to provide a composition adapted for topical application to animal tissue.

7. A germicidal iodine composition as defined in claim 6, wherein adjuvants are selected to provide a composition adapted for use as a hand washing composition.

8. A germicidal iodine composition as defined in claim 6, wherein adjuvants are selected to provide a composition adapted for use as a bovine teat dip.

9. A germicidal iodine composition as defined in claim 1, wherein the iodide ion concentration is in the range of about 0.05% to 0.5% and the iodate ion concentration is in the range of about 0.005% to 0.2%.

10. A germicidal composition as defined in claim 1, wherein the iodine concentration is about 0.01 to 0.1%, the iodide ion concentration is about 0.05 to 0.5%, the iodate ion concentration is about 0.05 to 0.1%, and the pH is within the range of pH 5.5 to 6.5.

* * * * * to# REEXAMINATION CERTIFICATE (76th)

United States Patent [19]

Winicov et al.

[11] B1 4,271,149

[45] Certificate Issued    Apr. 19, 1983

[54] GERMICIDAL IODINE COMPOSITIONS WITH ENHANCED IODINE STABILITY

[75] Inventors: Murray W. Winicov, Woodside, N.Y.; Michael Oberlander, Kansas City, Mo.

[73] Assignee: West Agro-Chemical, Inc., Westwood, Kans.

Reexamination Request
No. 90/000,179; Mar. 26, 1982

Reexamination Certificate for:
Patent No.: 4,271,149
Issued: Jun. 2, 1981
Appl. No.: 77,787
Filed: Sep. 21, 1979

[51] Int. Cl.$^3$ .................... A01N 59/12; A61K 31/74
[52] U.S. Cl. ......................... 424/150; 424/78; 424/80
[58] Field of Search ........................ 424/78, 80, 150

[56] References Cited

U.S. PATENT DOCUMENTS

| | | | |
|---|---|---|---|
| 1,280,580 | 10/1918 | Swett | 424/150 |
| 1,925,135 | 9/1933 | Chandler | 424/150 |
| 1,964,518 | 6/1934 | Karns | 424/150 |
| 2,386,252 | 10/1945 | Mendelsohn | 424/150 |
| 2,918,400 | 12/1959 | Looman | 424/150 |
| 2,987,505 | 6/1961 | Werner | 424/150 |
| 3,274,116 | 9/1966 | Mills | 252/106 |
| 3,282,777 | 11/1966 | Ceriotti | 424/150 |
| 3,288,708 | 11/1966 | Cordle et al. | 424/150 |
| 3,644,650 | 2/1972 | Sabatelli et al. | 424/150 |
| 4,113,857 | 9/1978 | Shetty | 424/150 |
| 4,288,428 | 9/1981 | Föll et al. | 424/150 |
| 4,297,232 | 10/1981 | Ruben et al. | 424/150 |

FOREIGN PATENT DOCUMENTS 414951    12/1966    Switzerland ................... 424/78

OTHER PUBLICATIONS

Clippinger et al., "Electrometric Indicators with the Dead-stop End-Point System, Application to Neutralization and Precipitation Reactions", *Industrial Eng. Chem.* Analytical Edition, 1939 pp. 216 et seq.

*Primary Examiner*—Douglas W. Robinson

[57] ABSTRACT

New and improved germicidal iodine compositions are provided in which iodine levels, in the presence of organic adjuvants containing at least carbon, hydrogen and oxygen atoms, are maintained for extended periods of time in the presence of iodide, through the addition of iodate and control of pH within the range of pH 5–7.

REEXAMINATION CERTIFICATE ISSUED UNDER 35 U.S.C. 307.

NO AMENDMENTS HAVE BEEN MADE TO THE PATENT.

AS A RESULT OF REEXAMINATION, IT HAS BEEN DETERMINED THAT:

The patentability of claims 1–10 is confirmed.

* * * * *